US009487394B2

(12) United States Patent
Yu

(10) Patent No.: US 9,487,394 B2
(45) Date of Patent: *Nov. 8, 2016

(54) METHODS FOR FABRICATING MICRO-DEVICES

(71) Applicant: ANPAC BIO-MEDICAL SCIENCE CO., LTD., Road Town (VG)

(72) Inventor: Chris Yu, Conneautville, PA (US)

(73) Assignee: Shanghai Xinshenpai Technology Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/292,396

(22) Filed: May 30, 2014

(65) Prior Publication Data

US 2014/0299574 A1    Oct. 9, 2014

Related U.S. Application Data

(62) Division of application No. 12/707,731, filed on Feb. 18, 2010, now Pat. No. 8,828,246.

(51) Int. Cl.
*B81C 1/00* (2006.01)
*A61M 37/00* (2006.01)
(Continued)

(52) U.S. Cl.
CPC ....... *B81C 1/00341* (2013.01); *B81C 1/00119* (2013.01); *A61M 37/0015* (2013.01); *A61M 2037/0053* (2013.01); *B01L 3/502707* (2013.01); *B81B 2201/058* (2013.01);
(Continued)

(58) Field of Classification Search
CPC ....... H01J 9/025; H05K 3/108; H05K 3/083; B81C 1/00119; B81C 1/00341; B01L 3/502707; B81B 2201/058; B82Y 5/00; A61M 2037/0053; A61M 37/0015

USPC ........ 216/17, 19, 27, 33, 39, 40, 41, 79, 80; 438/21, 619, 691
See application file for complete search history.

(56) References Cited

U.S. PATENT DOCUMENTS 6,322,202 B1 * 11/2001 Ahn ................... B41J 2/14064
                                                       216/27
6,602,791 B2    8/2003  Ouellet et al.
8,159,107 B2 *  4/2012  Stalford ............... B81B 3/0024
                                                       310/306
(Continued)

FOREIGN PATENT DOCUMENTS

JP      2006-100456    4/2006
WO      WO 97/21090    6/1997
(Continued)

*Primary Examiner* — Lan Vinh
(74) *Attorney, Agent, or Firm* — Weisun Rao; Greenberg Traurig, LLP

(57) ABSTRACT

The present invention provides methods utilizing current nano-technological processes for fabricating a range of micro-devices with significantly expanded capabilities, unique functionalities at microscopic levels, enhanced degree of flexibilities, reduced costs and improved performance in the fields of bioscience and medicine. Such fabricated micro-devices have significant improvements in many areas over the existing, conventional methods, which include, but are not limited to reduced overall costs, early disease detection, targeted drug delivery, targeted disease treatment and reduced degree of invasiveness in treatment. Compared with existing, conventional approaches, the said inventive approach disclosed in this patent application is much more microscopic, sensitive, accurate, precise, flexible and effective.

6 Claims, 30 Drawing Sheets

(51) Int. Cl.
*B01L 3/00* (2006.01)
*B82Y 5/00* (2011.01)

(52) U.S. Cl.
CPC .............. *B81B 2201/06* (2013.01); *B82Y 5/00* (2013.01); *Y10T 29/49124* (2015.01)

(56) References Cited

U.S. PATENT DOCUMENTS

| | | | |
|---|---|---|---|
| 8,440,093 B1 * | 5/2013 | Nassef | B01L 3/502707 216/84 |
| 2003/0186474 A1 * | 10/2003 | Haluzak et al. | 438/21 |
| 2004/0106914 A1 * | 6/2004 | Coppeta et al. | 604/892.1 |
| 2004/0202994 A1 * | 10/2004 | Timperman | 435/4 |
| 2006/0216740 A1 * | 9/2006 | Edman et al. | 435/6 |
| 2009/0026561 A1 * | 1/2009 | Reichenbach et al. | 257/416 |

FOREIGN PATENT DOCUMENTS

| | | |
|---|---|---|
| WO | WO 01/35928 | 5/2001 |
| WO | WO 01/43876 | 6/2001 |
| WO | WO 01/64344 | 9/2001 |
| WO | WO 2007/106557 | 9/2007 |
| WO | WO 2007/122552 | 11/2007 |

\* cited by examiner

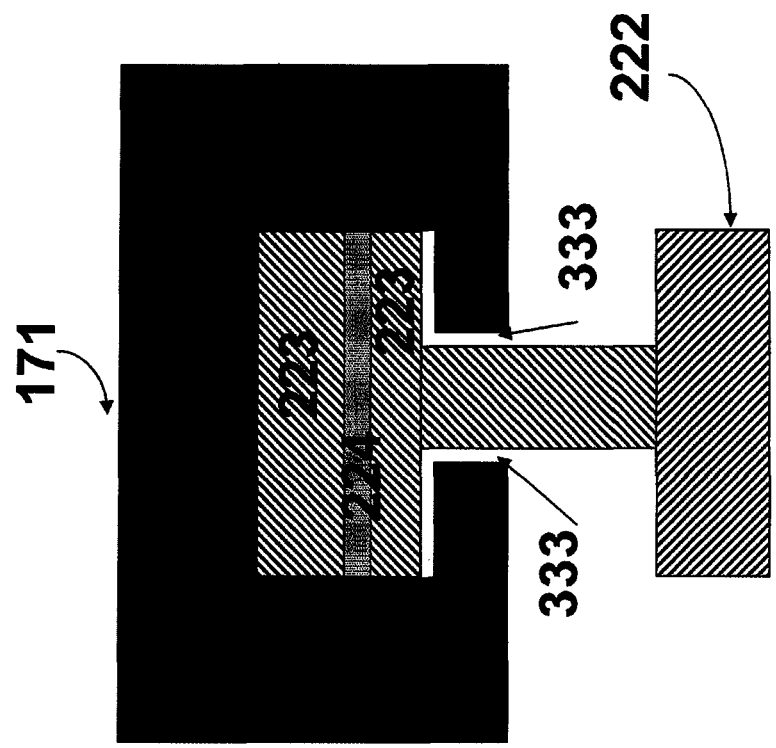

METHODS FOR FABRICATING MICRO-DEVICES

CROSS-REFERENCE TO RELATED APPLICATION

This is a divisional application of and claiming priority from U.S. application Ser. No. 12/707,731, filed on Feb. 18, 2010, the contents of which are incorporated herein by reference in their entireties.

BACKGROUND OF THE INVENTION

While progress has been made in the fields of modern bio-science and medicine in the past few decades, basic methodologies, approaches and, to the largest extent, instruments in the above mentioned areas have remained fundamentally the same. This has resulted in a relative lack of major breakthroughs in key areas such as early deadly disease detection (i.e., cancer), effective and targeted drug release and effective disease treatments. As an example, treatment options for cancer, heart disease and diabetes still remain limited.

For example, various imaging techniques such as nuclear magnetic resonance ("NMR") and computerized tomography scans ("CT Scans") have been developed to better diagnose diseases via their improved resolutions. In the field of cancer detection, recently emerging detection processes involve the use of an immunological approach with tissue-specific gene expression identification targeting processes which utilize the aid of technologies such as micro-electro-mechanical systems ("MEMS"). See K. Patel, et al., Nature Reviews, Vol. 8, pp 329 (2008). However, most of these techniques remain too macroscopic and lack a high degree of sensitivity and effectiveness for early stage detection of many deadly diseases such as cancer. At best, the usefulness of these techniques is limited to certain forms of diseases and to very limited locations within the human body, at the mid to late stages of disease. While newer detection technologies utilizing an immunological approach and a tissue-specific gene expression identification targeting process mentioned above are being experimented for improved testing sample size, speed, and sensitivity, none of them has been clinically successful at identifying diseases such as cancer at an early stage with required sensitivity and specificity. Most of them require the use of complicated sample enrichment, marker chemistry, system calibration and/or data interpretation.

In the area of disease treatment for deadly diseases such as cancer, many current treatment techniques often lack effectiveness, selectivity and specificity. At the same time, many treatment approaches result in side effects. Specifically, for cancer treatment, most of the common approaches including radiation, chemotherapy, surgery and a combination of the above technologies have not been effective for many types of cancer at the mid to late stages of the cancer, have significant side effects and lack specificity to targeted cancerous areas and cells. In addition, cancer treatment is often very expensive. In cases where treatment is effective initially, cancer cells often develop resistance (especially with a number of platinum-based cancer drugs) and/or spread (metastasize) to other locations such as liver and lung. Recent experiments with angiogenesis inhibitor therapy, hyperthermia therapy, biological therapy and targeted treatments (see B. Zahorowska et al., J. Cancer Res Clin Oncol, published online (Jun. 17, 2009), for a review on targeted therapies) utilizing nano-particles for drug delivery and molecular modulated targeting using desired drugs or substance have shown some degree of promise. However, to date, none of these mentioned approaches have been fully proven in large sample clinical trials. Often, they introduce additional types of side effects such as the resulting of a compromised immune system.

One of the major challenges in the treatment of deadly diseases such as cancer is that drugs often cannot be effectively delivered to its intended target and/or sufficiently absorbed by the targeted cancer cells. Even if the drug has reached its intended target site and proven to be effective to diseased organs, tissues and cells, most of the drugs lack treatment selectivity, resulting in damage to normal organs, tissues, and cells as well as the resulting undesirable side effects. In recent years, nano-technologies utilizing nano-sized particles ranging in size from 100 nanometers to a few microns have been proposed and evaluated for improved drug delivery performance. (See S. D. Smedt, J. Am. Chem. Soc. 130, pp. 14480-14482 (2008); A. L. Z. Lee, et al., Biomaterials, 30, pp. 919-927 (2009); T. Desai, Nano Lett. 9, pp. 716-720 (2009); R. O. Esenaliev, U.S. Pat. No. 6,165,440; P. S. Kumar, et al., U.S. Pat. No. 7,182,894; C. J. O'Conner, et al., US Patent Application Publication No. 2002/0068187; S. A. Herweck, et al., US Patent Application Publication No. 2004/0236278; H. Hirata, et al., US Patent Application Publication No. 2007/0243401; G. S. Yi, et al., US Patent Application Publication No. 2009/008146).

Most of the proposed approaches using nano-particles cited above lack the following basic functions and abilities: (a) to reach its targeted location in a controlled manner, (b) selectivity and specificity to its intended targets (such as cancer cells), (c) the ability to avoid interactions with the environment on its way to its intended target(s), (d) a controlled release mechanism at a microscopic level (for example, releasing drug only to a specific cell and not to its surrounding area), and (e) bio-degradability of the nano-particle after its use. Very few have contemplated approaches which selectively target treatment sites. A. Chauhan, et al., disclosed a drug delivery system comprising a contact lens in which nano-particles are dispersed with drug encapsulated within said nano-particles (See US Patent Application number 20040096477). J. S. Minor, et. al. (US patent application number 20060040390) proposed the use of a biological "key" molecule to recognize targets. A. Manganaro, et al. proposed a method (US patent application number 20080279764) in which an ascorbate on the surface of nano-carrier is used to react with the super oxides produced by the cells, with an expected result of enhanced reactions between anti-cancer agent in the carrier and the cancer cells. While the above mentioned prior art attempts to target treatment, the applicability is relatively narrow and lacks the ability to target a wide range of cells, tissues, organs and diseases. Further, the "key" molecule or ascorbate on the surface of nano-carriers mentioned in the Minor application and the Manganaro application are likely to react with the environment in the living body and will thus have many difficulties in reaching its intended targets while still in its original form.

While the above-cited approaches have shown some potential merits over conventional approaches, they have not fundamentally solved the controllability, selectivity and specificity problems in drug delivery. For example, nano-particles coated with a designed drug onto their surface do not necessarily prevent the drug from interacting with various bio-chemical systems along their way to the targeted delivery location; nor do they have the intrinsic capabilities of selective delivery to diseased organs, tissues or areas within the body.

In recent years, certain types of micro-chips such as MEMS have been utilized for a number of bio-medical related applications. However, most of these applications involve relatively simple micro-chips with limited functions and for relatively narrowly focused applications in the field of bio-medicine. Mainly, these applications are limited to imaging (for example, Durack, U.S. Pat. No. 7,590,221), sensing (for example, Liu, et al., U.S. Pat. No. 7,661,319) and genomics related analysis and mapping (for example, Harris, et al., U.S. Pat. No. 7,635,562). Novel device fabrication processes disclosed in this patent application for bio-medical applications using microelectronics processes are clearly differentiated from the prior art cited above in unique process flows, utilization of the most advanced microelectronics processing technologies, degree of integration, and ability to fabricate devices with a much higher degree of functionality and flexibility.

To overcome the above-mentioned, long unresolved problems, a new and novel method utilizing current nano-technological processes for fabricating a range of micro-devices with significantly expanded capabilities, unique functionalities at microscopic levels, an enhanced degree of flexibilities, reduced costs and improved performance in the fields of bioscience and medicine is disclosed in the within patent application. Micro-devices fabricated using the disclosed nano-technological techniques have significant improvements in many areas over the existing, conventional methods. Such improvements include, but are not limited to, reduced overall costs, early disease detection, targeted drug delivery, targeted disease treatment and reduced degree of invasiveness in treatment. Compared with existing, conventional approaches, the said inventive approach disclosed in this patent application is much more microscopic, sensitive, accurate, precise, flexible and effective. This novel approach is able to deliver a superior level of performance in medical treatments over the existing modalities.

While microelectronic processes have been used for fabricating integrated circuit ("IC") devices such as microprocessors, digital signal processors ("DSP") and memory chips for the past two to three decades, their use has not been extended to most areas of bioscience and medicine. While there have been some application of micro-chips used in the area of laboratory diagnostic tests such as gene/DNA mapping and potential tests for diseases, their meaningful application in the areas of in-vivo diagnosis, drug delivery and disease treatments have not been utilized and are basically non-existent in the current state of the art.

SUMMARY OF THE INVENTION

In this invention, novel methods for fabricating new types of micro-devices for biological and medical applications are disclosed. These novel methods employ microelectronics process technologies and novel process flows to fabricate micro-devices that have improved performance, flexibility and the ability for disease detection and treatment at microscopic levels. These micro-devices have reduced costs over the conventional methodologies and vehicles found in current medical treatment modalities.

Said micro-devices include, but are not limited to, micro-containers and micro-injectors for drug delivery and disease treatments which are disclosed in U.S. patent application Ser. Nos. 12,416,280 and 12,498,698 by Yu, et al. The underlying microelectronics process technology concept is disclosed in the text of Stanley Wolf's treatise, "Silicon Processing For The VLSI ERA", Volume 1, Lattice Press (2000). The microelectronics processes include, but are not limited to, thin film deposition, lithography, etch (both wet and dry etch processes), cleaning, wet processing, diffusion, ion implantation and chemical mechanical polishing ("CMP") processes. Such processes are utilized and arranged in many novel ways to fabricate various types of micro-devices with a minimum feature size as small as 0.1 micron. The above-mentioned micro-devices have at least one and may include multiple functions with typical sizes ranging from sub-microns to several millimeters. With the advancement of microelectronics technologies, the ability to fabricate even smaller features (i.e. features smaller than 10 nm) is fully expected in the near future.

One embodiment of such novel method is the process flow for fabricating micro-containers using microelectronics processes. Another embodiment is the process flow for making micro-injectors. Both of them can be used for drug delivery, diagnosis, disease prevention (for example, transporting useful biological agents such as messenger RNA, hormone, or catalysts from one part of the living body to another location in the body) and other disease treatment applications. Another inventive aspect of this application is a set of fabrication process flows which integrate micro-injectors and micro-containers on the same micro-device to achieve controlled, accurate and flexible compound release. The injection action can be triggered by forces, which include, but are not limited to, electrical, electro-magnetic, hydraulic, electro-mechanical, micro-electro mechanical, capacitive and piezoelectric forces. Yet another novel aspect of the invention is a process flow utilizing microelectronics processes for fabricating micro-devices containing micro-containers and injectors integrated with an integrated circuit and other components, which include, but are not limited to, micro-sensors, signal receivers, signal transmitters, positioning devices and motion apparatus (such as micro-motors and micro-propellers) with functions for carrying desired drug(s), positioning (for example, with a motorized propeller), sensing, receiving and transmitting signals in a wireless manner, logic processing, decision making, selectively targeting diseased locations and injecting desired drugs into the targeted locations. These processes include integration of complementary metal-oxide-semiconductor ("CMOS") or bipolar complementary metal-oxide-semiconductor ("BiCMOS") devices and circuits with various components such as micro-containers, injectors and propellers. One additional innovative aspect of the current application is the ability to select micro-containers for compound release through pre-programmed instructions from an integrated circuit on the micro-device or for receipt of instructions from a host computer to the corresponding selected injectors. Still, another novel aspect of this invention is the use of micro-containers and injectors for delivering desired drugs or compounds with improved efficiency, selectivity and specificity which correspond to reduced side effects for patients as well as reduced costs. Another novel feature is that, in addition to drugs, the micro-containers and injectors can carry and deliver biological components carrying signals important for disease prevention and control, which include, but are not limited to, cells, proteins, hormones, catalysts, messenger RNA, receptors such as G protein linked receptors, and any desired biological, chemical and electrical species. More specifically, for cancer treatment, it is contemplated in this patent application that in addition to cancer killing, synthesized drugs, natural or synthesized human cells and/or proteins capable of killing tumors and triggering resistance to cancers such as T cytotoxic cells ("CD8 T cells"), Natural Killer ("NK") cells, Type II Interferons, and tumor necrosis factors ("TNFs") be carried by the micro-containers to intended locations and/or to targeted cells for improved treatment effects.

A number of definitions will be discussed here. For the micro-devices fabricated using the novel microelectronics process flows disclosed in this patent application for biological and medical applications, it is often required that at least one component be movable upon application of a force or an energy (for example, a probe head can expand out of the surface of a micro-device surface and probe its surrounding area, when an electrical voltage is applied to the piezoelectric base of the said probe). Also, optionally, there is at least one space region in which one component in the micro-device can move (for example, an injector base which can move in an open region below a micro-container). Finally, in all micro-devices, there are permanent structures made of various materials (for example, the substrate of a micro-device). To achieve the above stated functions, various types of materials are required in the fabrication of the micro-devices. Based on their roles for achieving the above-stated functions (movable component, permanent structure, and space region), the materials are classified as either "movable material", "structural material" or "space material." "Movable material" is a material which is used to form the component which can move upon application of a force or energy in the micro-device. Sometimes, after the micro-device is fabricated, a portion of the movable material is movable while other portion of the movable material may be fixed and immobile. "Structural material" is a material which (at least part of it) will permanently remain in the micro-device. Finally, "space material" is a material which is initially used to occupy and define a space, and later on, in the fabrication process, it will substantially be removed to form said space.

The word "compound" used in this application generally means an item or combination of items which can be carried in a container. It can be a drug, an enzyme, a messenger RNA, a liquid chemical, or other similar liquid component.

Often, in an etching process, one material (for example, a material A deposited on a substrate B) needs to be etched off while another material needs to remain (in this example, the substrate B). To achieve this, the etch process is required to have a higher etch rate for one material (material A in this case) over another material (substrate B in this case). The above stated requirement (or feature) can often be stated that material A is "selective" to material B, or, the etch process is "selective" for material A over material B.

Another key aspect which should be discussed here is the facts that since micro-devices fabricated using the novel processes disclosed in this patent application will be used both in vitro and in vivo, depending the type of micro-device, it is important that such micro-devices are packaged using materials compatible with living systems (such as blood, tissue, organs, etc.). Such compatible materials include, but are not limited to, inorganic and polymer materials which are inert and cause no harm to a living body, and natural or synthesized bio-materials. For example, for inorganic materials, silicon, polysilicon, silicon nitride, silicon oxynitride, silicon carbide, and silicon dioxide are inert when placed within a living system. Since the above mentioned inorganic materials are also widely used in microelectronics, they are ideal materials for micro-device fabrication processes disclosed in this patent application. In addition, micro-devices will be sealed in packaging materials so that materials within the micro-device do not get exposed to the living body, further insuring safety in using such micro-devices in vivo. For the micro-devices fabricated using the inventive microelectronics processes, another feature includes the option of self disintegration or timed disintegration of micro-devices, in which micro-device can disintegrate into smaller pieces, preferably smaller than 1 micron in size, after its use in the living body.

BRIEF DESCRIPTION OF THE DRAWINGS

These and other features, aspects and advantages of the present invention will become better understood with regard to the following description, appended claims and accompanying drawings where:

DETAILED DESCRIPTION OF THE INVENTION

Figure 1:
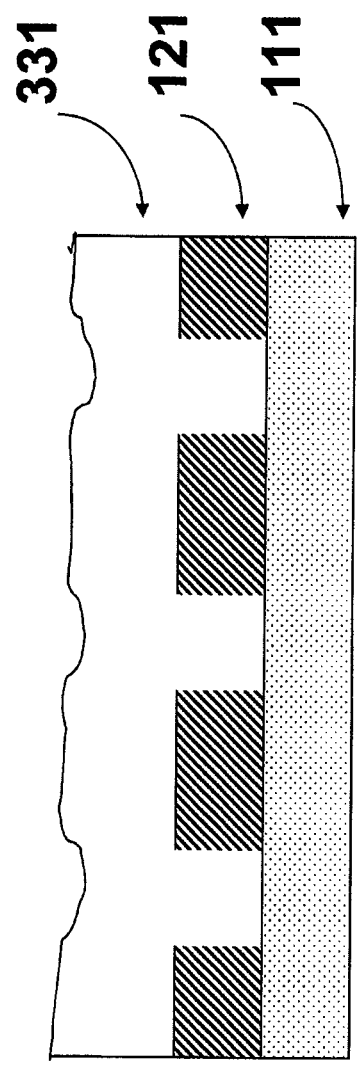
FIGS. 1 through 4 (FIG. 1, FIG. 2, FIG. 3 and FIG. 4) illustrate an innovative method of fabricating micro-containers for carrying compounds for bio-medical applications.

While major progress in the area of bio-medicine has been made in the past few decades, in a number of key areas including deadly disease (such as cancer) prevention, early detection and treatment, progress has been relatively slow. For example, to date, treatment options for cancer have remained mainly limited to chemotherapy, radiation treatment or a combination of the two. On the other hand, some progress has been made in the area of cancer curing drugs, including a targeted drug approach. However, drugs that have shown promise during animal testing have not performed as expected during clinical human trials. Often, drugs lack effectiveness, selectivity, specificity, have side effects and high costs. A new approach and major innovation is urgently needed to address these major issues. In this invention, a set of novel process flows utilizing microelectronics processes to fabricate powerful micro-container/injectors with other optional components integrated onto integrated circuits for improved drug and other agent transportation and delivery with improved effectiveness, selectivity and specificity with reduced side effects and costs. A novel use of these devices is further disclosed herein.

While microelectronics process technology has been utilized to fabricate a wide range of information technology-related products such as memory devices, micro-processors, and digital signal processors, relatively speaking, its application in the field of bio-medicine is still in its infancy. To date, the application of microelectronics process technologies has been mainly limited to chips for lab tests such as DNA mapping and the diagnosis of certain diseases. Such chips contain integrated, miniaturized probes to speed up tests and data collection. However, to a large extent, its (microelectronics) application and associated special fabrication process flows for more sophisticated bio-medical applications have not been developed.

The key inventive aspect of this patent application is a set of novel process flows using microelectronics processes for fabricating micro-devices comprising at least a sealed space and a micro-component which can convert an applied force or energy into a motion, where a portion of the wall of said sealed space is a part of said micro-component. The microelectronics process includes, but is not limited to, thin film deposition, lithography, wet etch, dry etch, cleaning, wet processing, diffusion, ion implantation, annealing and CMP.

One embodiment is the fabrication process of micro-containers and micro-injectors for bio-medical applications with significantly improved drug carrying flexibility, selectivity, specificity, efficiency, and reduced side effects and costs.

Another key, novel aspect of the current invention is the fabrication process flow to integrate micro-injectors and micro-containers with an injection action from the said injector to release drug(s) or agent(s) contained in the micro-containers.

Yet another novel feature of this disclosure is the integration of micro-containers, injectors, and other components which include, but is not limited to, sensors, position sensors, signal transmitters, signal receivers and motion apparatus (such as motorized propellers and steppers) with integrated circuits onto the same micro-device. These features use processing technologies which include, but are not limited to CMOS or BiCMOS technologies with both memory and logic functions. The integration of the above components can greatly enhance performance of the micro-devices for bio-medical applications, with both mechanical abilities as well as device motion, position, signal sensing, signal transmission, data storage, data analysis, data processing and logic decision-making capabilities.

One additional innovative aspect of the current application is the ability to select micro-containers for drug (or agent) release through a pre-programmed instruction set or instructions from an integrated circuit on the micro-device or a host computer via wireless signal instructions to the corresponding, selected micro-device.

Another embodiment is the process flow and design using a bio-compatible material with dissolution ability in a desired environment, as a capping layer for micro-containers for timed drug or carrying agent release.

Still, another embodiment is the use of micro-containers/injectors for carrying natural and/or synthesized cells, proteins, biological, chemical, and electrical species for disease prevention and treatment. The agents carried are not limited to drugs. The agents could be species carrying biological signal information and immunity triggering agents, hormones, catalysts, messenger RNA, receptors such as G protein linked receptors, which have improved speed and efficiency. For example, for cancer prevention and treatment, natural tumor killing or signal carrying cells/proteins can be carried to further efficiency and speed (such as CD8 T cells, NK cells, Type II Interferons, and TNFs).

In this invention disclosure, the micro-devices include, but are not limited to, micro-containers and micro-injectors for drug delivery and disease treatments. Other components include sensors, signal transmitters, signal receivers and motorized propellers. The components/devices can be integrated onto integrated circuits with both memory and logic functions. The said microelectronics processes include, but are not limited to, thin film deposition, lithography, etch (both wet and dry etch processes), cleaning, wet processing, diffusion, ion implantation and CMP processes. Such processes are utilized and arranged in many novel ways to fabricate various types of micro-devices with a minimum feature size of as small as 0.1 micron. The above-mentioned micro-devices have one to multiple functions, with typical sizes ranging from sub-micron to several millimeters. Optionally, the said devices are bio-degradable, or capable of disintegrating into smaller pieces on the order of less than 10 microns.

Figure 2:
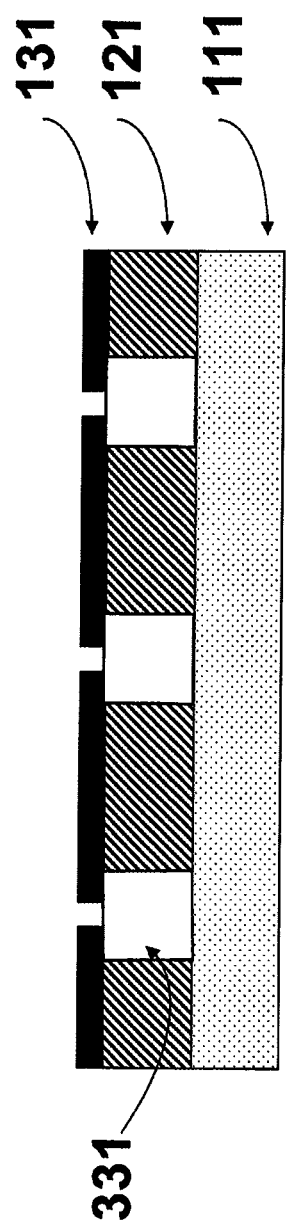
Figure 3:
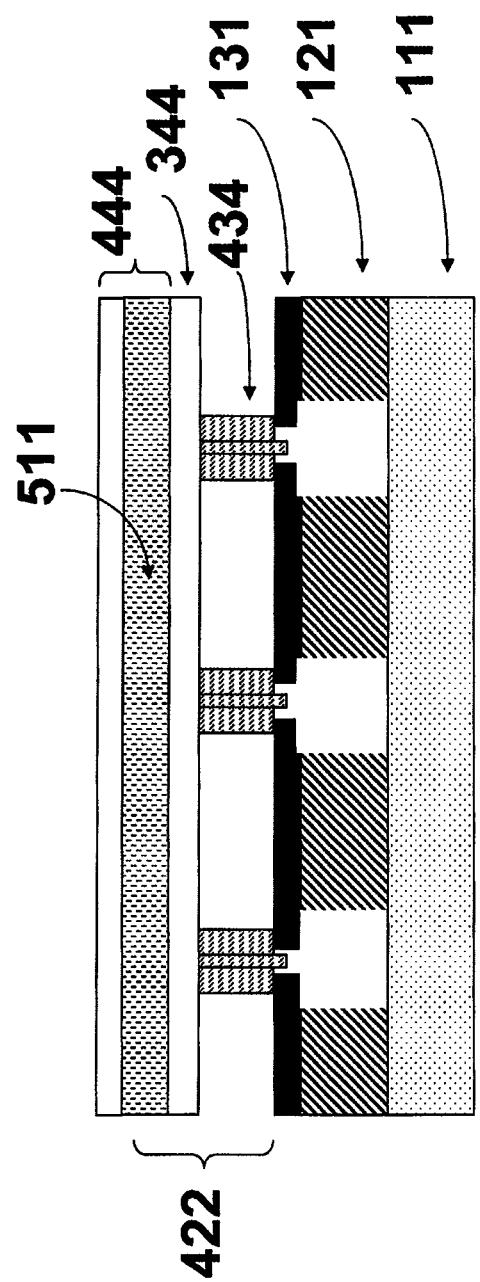
Figure 4:
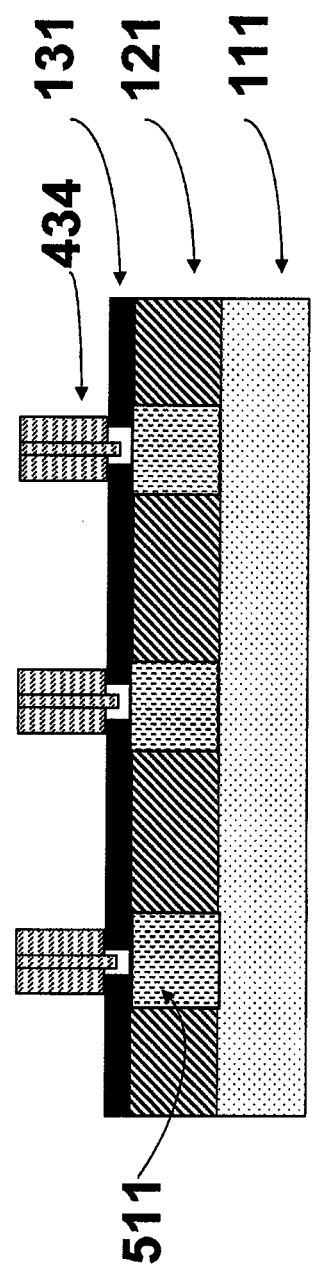

FIG. 1 through FIG. 4 show the first example of a novel process flow for fabricating micro-containers using microelectronics processes. In FIG. 1, a structural material 121 is first deposited onto a substrate 111. Said structural material 121 is deposited via chemical vapor deposition, sputtering, vacuum evaporation, or other suited methods, with chemical vapor deposition preferred due to its high deposition rate and maturity. Substrate 111 can be a semiconductor material such as silicon, silicon based compounds, non-conductive inorganic materials, non-conductive organic or biological material, with silicon or polysilicon materials preferred. Structural material 121 is next patterned using lithography and etch processes, with a desired set of patterns such as holes formed in the structural material 121. Structural material 121 preferably has a reasonably higher etch rate in the desired etch process than that of substrate material 111, so that the etch process can stop and leave the substrate 111 unaffected. The structural material 121 can be silicon nitride, silicon oxynitride, silicon carbide, or other materials with a different etch rate than that of substrate 111 in the desired etch process. The dimension of the patterned holes in structural material 121 should be the desired micro-container dimension since it will be the micro-container when the fabrication process is completed. A space material 331 is next deposited, filling in the holes defined in the previous step. The space material 331 is a sacrificial material since it will be removed at a later process. It can be an inorganic material such as silicon dioxide ($SiO_2$), with a high etch selectivity to substrate 111 and structural material 121 (it is required to have a reasonably higher etch rate than those of substrate 111 and structural 121). After deposition of space material 331, as shown in FIG. 1, there is a topography due to recessed areas in the layer of structural material 121. Therefore, chemical mechanical polishing is used to remove space material 331 above the structural material 121, leaving space material 331 remaining in the holes in layer 121 at the same height as the surface of structural material 121, as shown in FIG. 2. A structural material 131, preferably with a reasonably slower etch rate than that of space materials 331 in desired etch chemistries, is subsequently deposited and patterned (via lithography and etch processes) to form small openings above the holes as shown in FIG. 2. Next, an etching process is used to remove space material 331 in the holes. The etch process is required to be selective to structural materials 111, 121, and 131, with space material 331 etched away only. The preferred etch processes are wet etch and vapor etch. For preferred SiO$_2$ as a space material 331, diluted FH solution can be used for wet etch and a vapor etching gas containing O$_2$ can be used in a vapor etch. Thus, micro-containers with a desired storage space and an opening are fabricated using this novel microelectronics process flow. Next, as shown in FIG. 3, the said substrate 111 with fabricated micro-containers with openings is micro-aligned with a compound filling station 422 which has compound filling nozzles 434, a compound reservoir 444, a desired compound 511, and a nozzle holder 344, and pressed against each other to have micro-nozzles 434 inserted into the openings of the micro-containers. As illustrated in FIG. 4, following the filling of a desired compound 511 into the micro-containers, the compound filling station 422 is detached, via etching of the nozzle holder 344 (again, a nozzle holder material 344 of SiO$_2$ and a vapor etching gas containing O$_2$ gas is preferred), from the said micro-container assembly, leaving nozzles 434 in the openings of the micro-containers. Thus, a set of micro-containers containing the said compound 511 with nozzles 434 can be fabricated using the above disclosed novel process flow as shown in the final step, FIG. 4.

Figure 5:
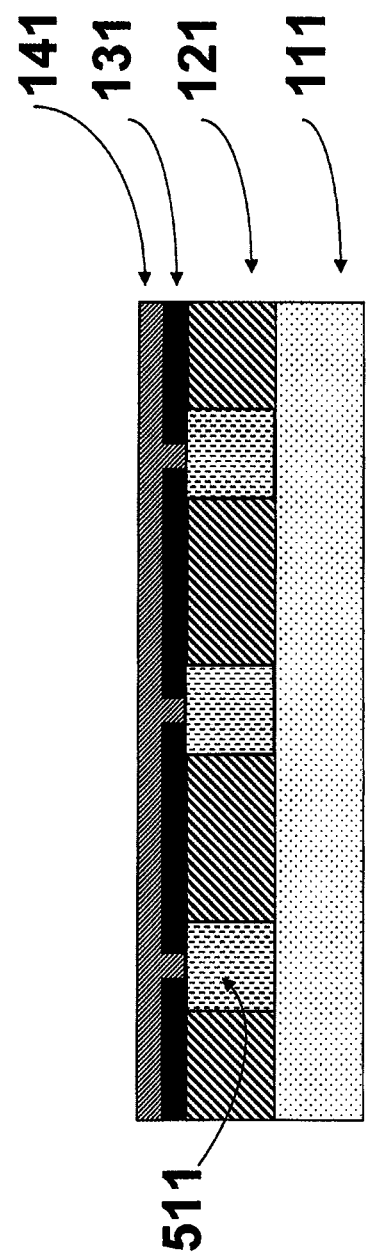
FIG. 5 shows an alternative process flow for fabricating micro-containers.

In addition to the above process flow illustrated in FIGS. 1-4, as a second example, an alternative process is shown in FIG. 5. After space material 331 removal and compound filling steps described above in FIG. 3, the filling station 422 is removed with nozzles 434 still attached to the station 422. A capping layer 141 is then deposited as illustrated in FIG. 5. The capping layer 141 is preferably a bio-compatible material which can be dissolved in an environment (for example, the human body) such as a blood environment for timed drug release.

Figure 6:
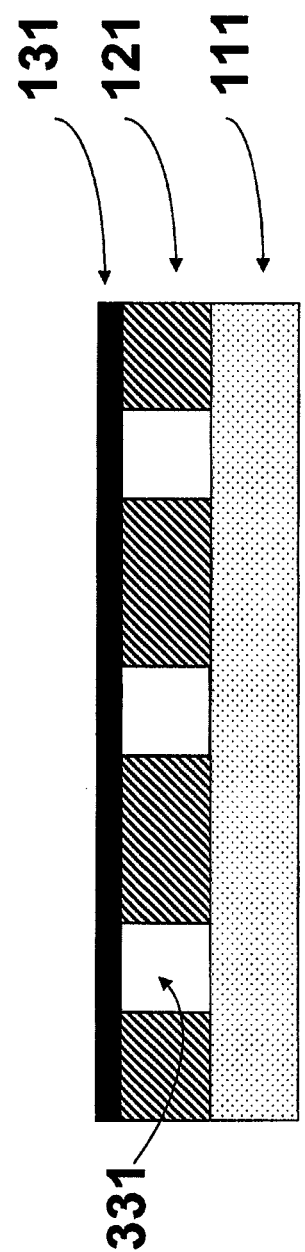
FIGS. 6 through 9 (FIG. 6, FIG. 7, FIG. 8, and FIG. 9) illustrate another novel process for fabricating micro-containers.
Figure 7:
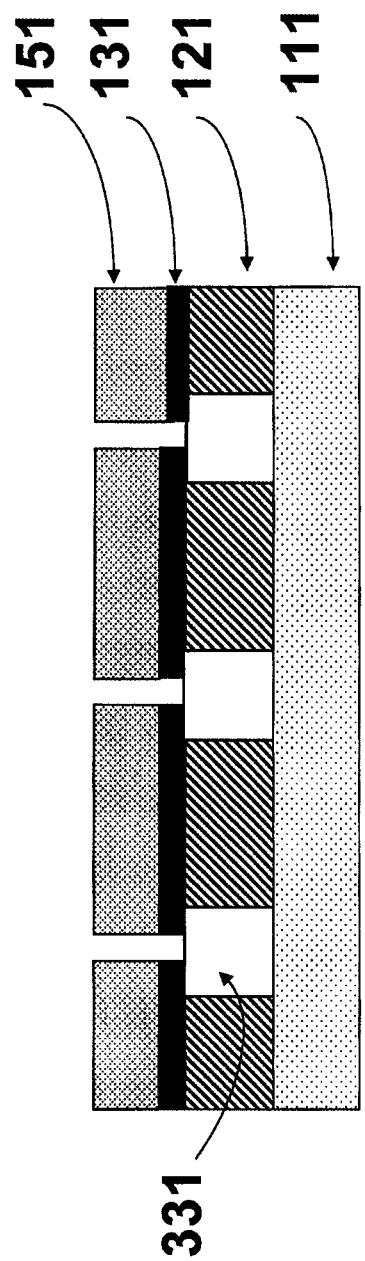
Figure 8:
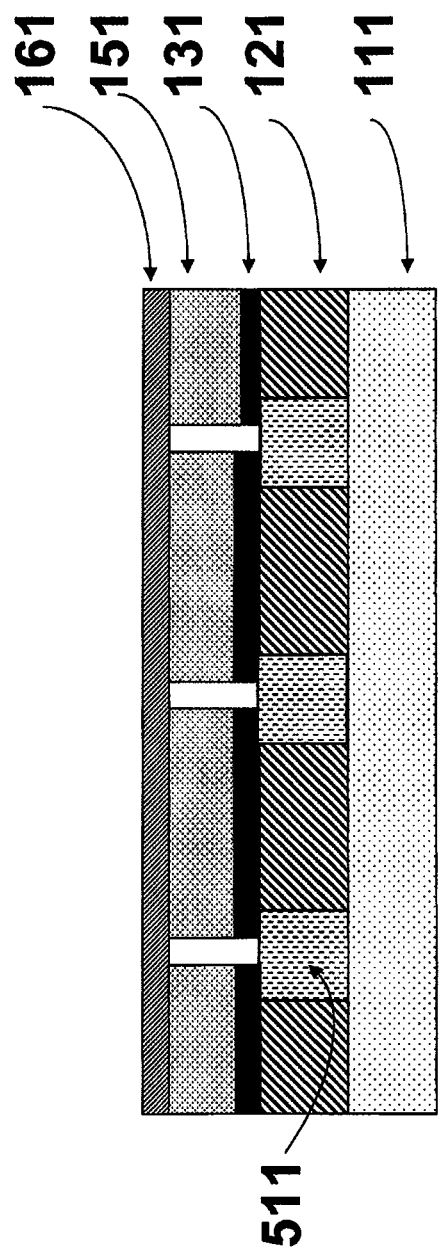
Figure 9:
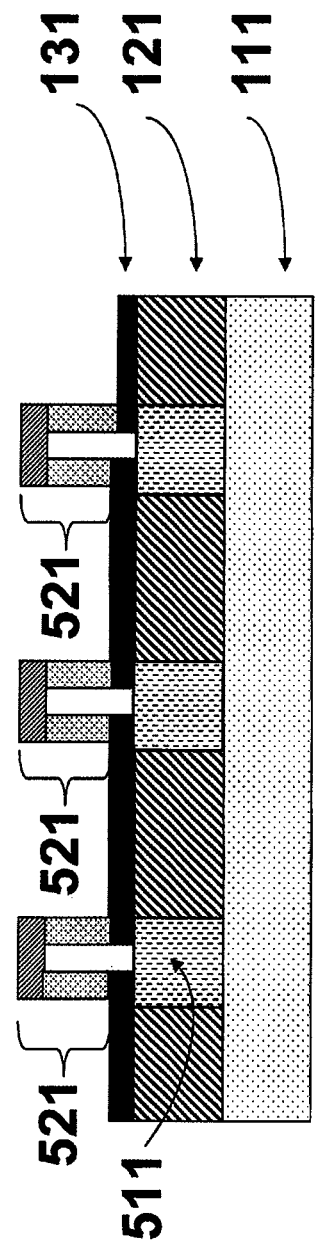

FIG. 6 through FIG. 9 show yet another novel, alternative process flow. Structural material 121 is deposited on a substrate 111 as shown in FIG. 1. Then, as shown in FIG. 6, following structural material 121 deposition, micro-container hole patterning in layer 121, space material 331 deposition and polishing, a first capping layer 131 is deposited. A thick capping layer 151 is next deposited, which is subsequently patterned using lithography and etch processes, along with the first capping layer 131, to form small openings above the hole regions in layer 121 as shown in FIG. 7. This etch process is selective to space material 331. Space material 331 is then etched, selective to other materials (111, 121, 131, and 151). Preferred process for etching space material 331 is wet or vapor etch. Finally, a desired compound (or compounds) is filled into the etched out micro-container holes as shown in FIG. 8. After fabrication of the said micro-containers, micro-nozzles can then be mounted onto the openings. Alternatively, the opening above the micro-container can be sealed with a top capping layer 161, as shown in FIG. 8, which can be a bio-degradable material capable of dissolving in a timed manner in a desired environment, such as in blood. Finally, the top capping layer 161 and the thick capping layer 151 can be patterned using lithography and etch processes to form sharpened nozzle heads 521 as illustrated in FIG. 9.

The above three examples show several novel process flows using microelectronics process technologies for fabricating micro-containers with compound such as drug carrying capabilities for bio-medical applications. The dimensions for an individual micro-container can range from 0.05 micron to 5 millimeters in size (diameter and height), with a minimum feature size (for example, for micro-container nozzle size) of 0.05 micron to 20 microns being preferred.

Figure 10:
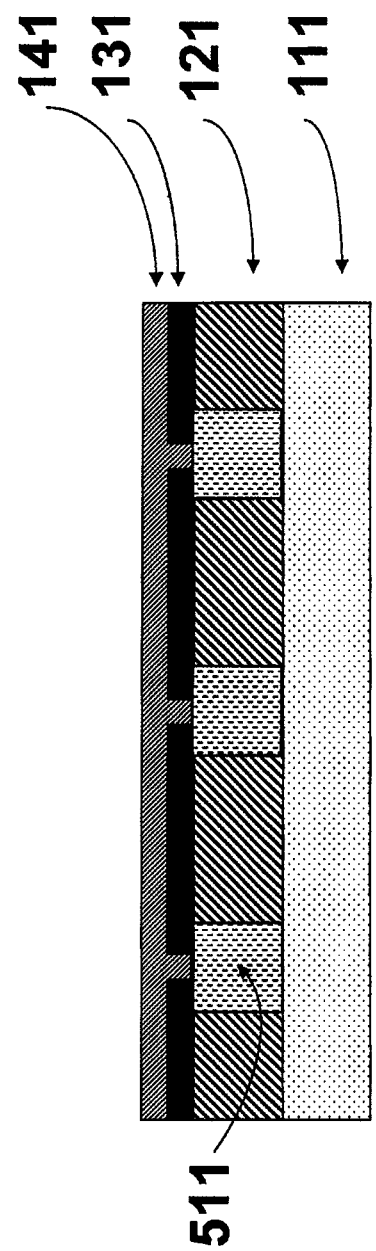
FIG. 10 and FIG. 11 illustrate a method of fabricating micro-containers for timed drug release using a bio-degradable capping (sealing) layer on the micro-container surface.
Figure 11:
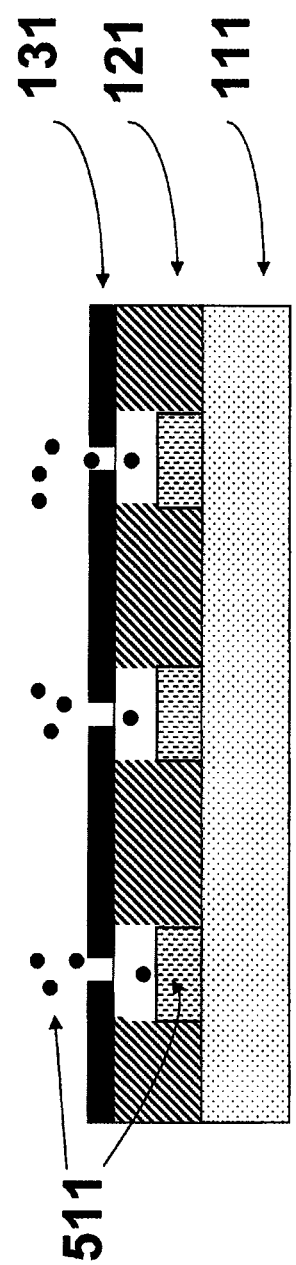

In addition to carrying a desired compound or compounds to a targeted location, when and how the said compound(s) are released is also critical for achieving the maximum effect. To address this matter, a novel approach combined with the disclosed micro-container is illustrated in FIG. 10. As shown in FIG. 10, a bio-compatible capping material 141 can be used to seal the narrow opening of the said micro-container following a desired compound 511 (or compounds) being filled into the container. The bio-compatible capping material 141 is selected such that it can dissolve in the environment along its way to the target or in the environment surrounding the target in a desired time frame, resulting in the timed release of compound(s) in the targeted area, as shown in FIG. 11. For example, it can dissolve in human blood, or an acid environment in the stomach all which can be manipulated depending on the desired therapeutic outcome. The timing is such that the narrow opening is opened in a desired time frame upon reaching its targeted location.

In some disease prevention or treatment applications, it may require a more precise, targeted delivery to an intended site, even at the cellular level. To achieve the above stated objective, one of the key inventive aspects of this patent application is to integrate micro-containers, injectors, sensors, positioning device, motion apparatus, communications devices, and other various components with one to multiple IC devices with memory and logic processing functions on the same micro-device to achieve far greater functionality, precision, selectivity, and flexibility than those by conventional drug delivery approaches, using microelectronics processes and disclosed process flows in this application. With the aid of sensors and IC device, an injector head can precisely attach to the targeted cells and not on the unintended cells, thereby greatly enhancing delivery selectivity, specificity and efficiency, with reduced side effects and costs over traditional approaches.

Using the novel microelectronics fabrication process flows disclosed in this application, micro-devices can be manufactured to store different types of compounds such as drugs and agents, and deliver and release the said different types of drugs and agents at desired locations, time intervals, sequence and drug doses. An array of micro-containers can be fabricated using the disclosed microelectronics processes with a desired spacing between adjacent micro-containers and container sizes, which can impact compound release dosage and density. Further, with the integration with an integrated circuit, each single micro-container, each single row of micro-containers, or any combination set of micro-containers can be selected to release stored compound. The above mentioned selective release function can also be achieved using the disclosed use of biocompatible and bio-degradable capping layer, where the thickness of bio-degradable capping layer can be varied to result in selective earlier release (using thinner bio-degradable capping layer) or selective delayed release (using thicker bio-degradable capping layer) of desired compound(s). Such a micro-device can be very powerful in releasing different types of drugs or agents at desired sequence and time interval, and combination of drugs at the targets (in-situ mixing), with effects which otherwise cannot be obtained with conventional disease treatment approaches.

One of the key novel aspects of this invention is the fabrication and resultant functions and mechanisms of micro-injectors. In one approach, a micro-container is integrated with a micro-injector housing at the bottom portion of the said micro-container. Such structures can be fabricated using novel microelectronics process flows disclosed below in FIG. 12 through FIG. 26. The mechanisms which can be used for micro-injectors include, but are not limited to, hydraulics, electro-magnetic, electrical, electro-mechanical, micro-electrical mechanical, capacitive and piezoelectric forces.

Figure 12:
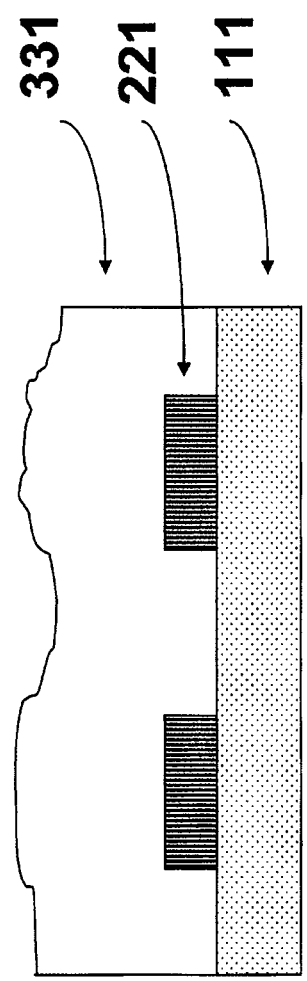
FIGS. 12 through 26 illustrate a novel method and process flow for fabricating integrated micro-injector and micro-container onto the same substrate, in which injection action using the integrated micro-injector is shown.
Figure 13:
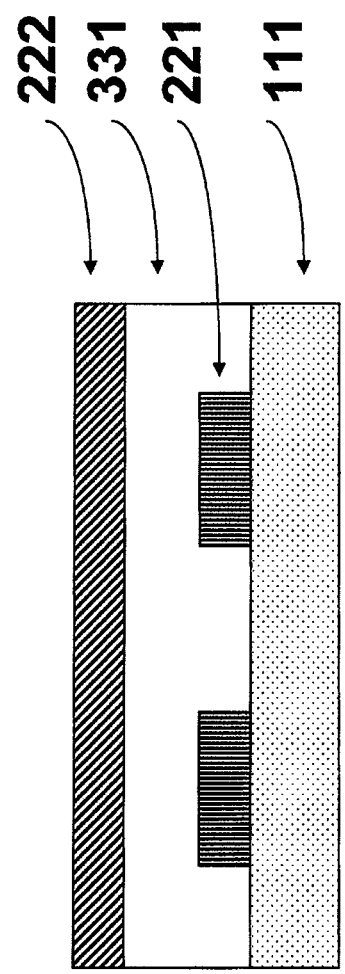
Figure 14:
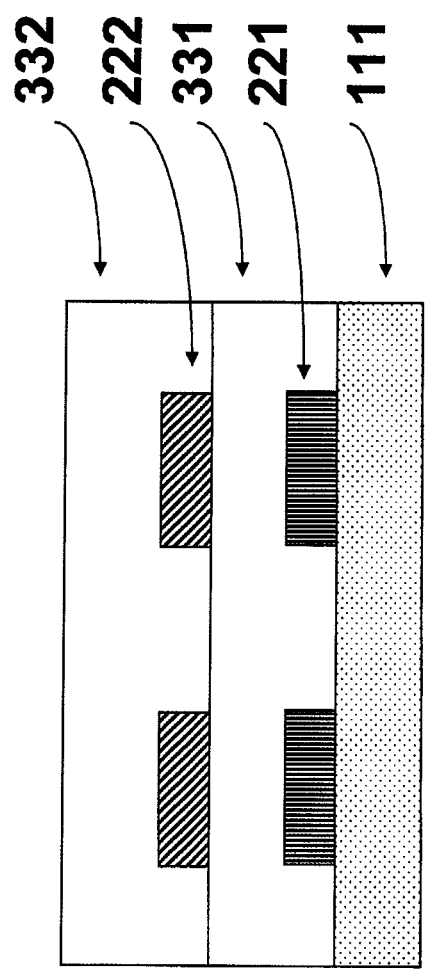
Figure 15:
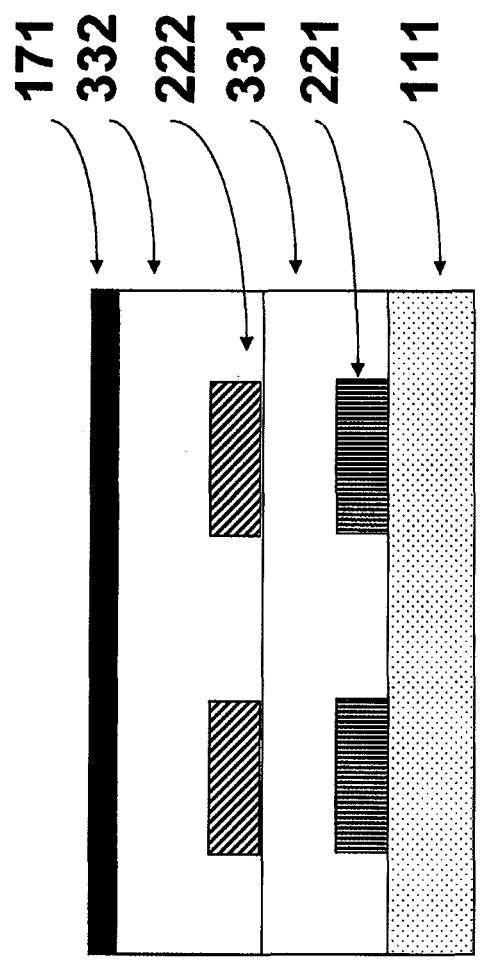
Figure 16:
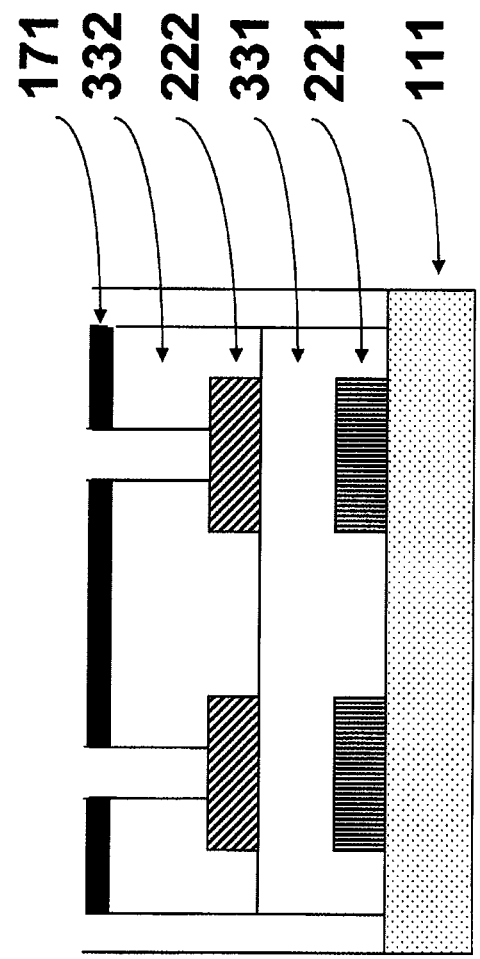

In addition to the above disclosed novel fabrication processes and process flows for making micro-containers and micro-injector mechanisms, yet another key embodiment of this application is how to fabricate integrated micro-injector and micro-container, as illustrated in FIG. 12 through FIG. 26. In FIG. 12, a movable material 221 is first deposited onto a substrate 111, and subsequently patterned using lithography and etch processes, forming a push plate which could later, when in use, apply a force onto the injector base plate for injection action. Optionally, an etch stop layer can be deposited onto the substrate 111 first to separate the substrate 111 and the movable material 221. The substrate 111 can be a silicon substrate, a silicon compound, or an inert material, while the movable material 221 can be polysilicon (when an etch stop layer is used between substrate 111 and movable material 221), silicon nitride, silicon carbide, or a desired material with sufficient mechanical strength. Next, a space material 331 is deposited (see FIG. 12), and planarized using chemical mechanical polishing (FIG. 13). The space material 331 is a sacrificial layer which will be removed later in the process, which can be a material such as silicon dioxide or aluminum oxide. As shown in FIG. 13 a movable material 222 is next deposited and patterned using lithography and etch processes which are illustrated in FIG. 14, forming an injector base plate, which will result in an injection action when a force is applied to it in operations. A second space material 332 is then deposited and planarized. The second space material 332 is preferably an identical material as the first space material 331 for ease of processing. Next, as shown in FIG. 15, a structural material 171 is deposited on top of the second space material 332. As illustrated in FIG. 16, layer 171 and space materials 332 and 331 are patterned using lithography and etch processes, selective to materials 111, 221, and 222, forming holes and trenches in layers of space materials 331 and 332.

Optionally, a thin layer of space material 333 is deposited (not shown in the figure), preferably by chemical vapor deposition or atomic layer deposition, which serves to help smooth injector motion later on. Space material 333 is preferably the same material as space material 332 for ease of removal in the same etching step later on.

Figure 17:
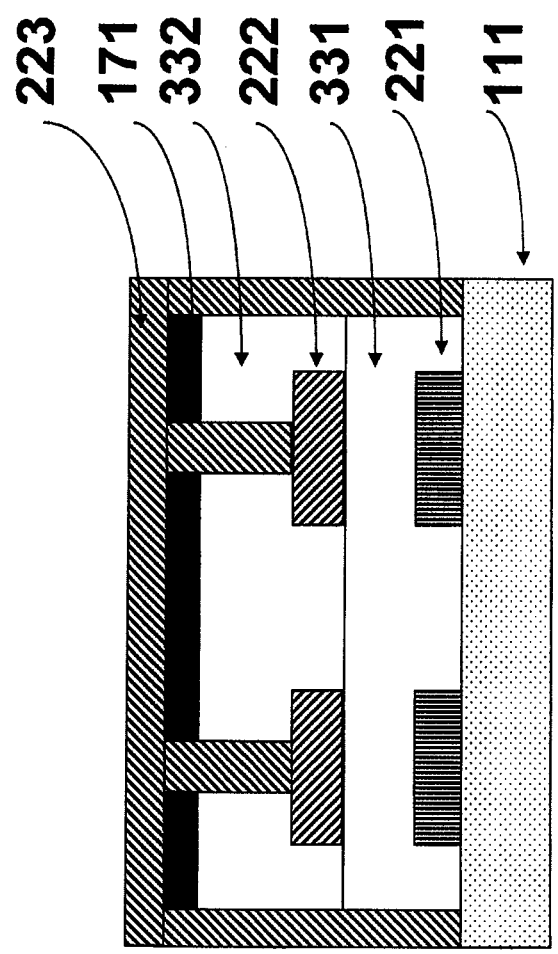
Figure 18:
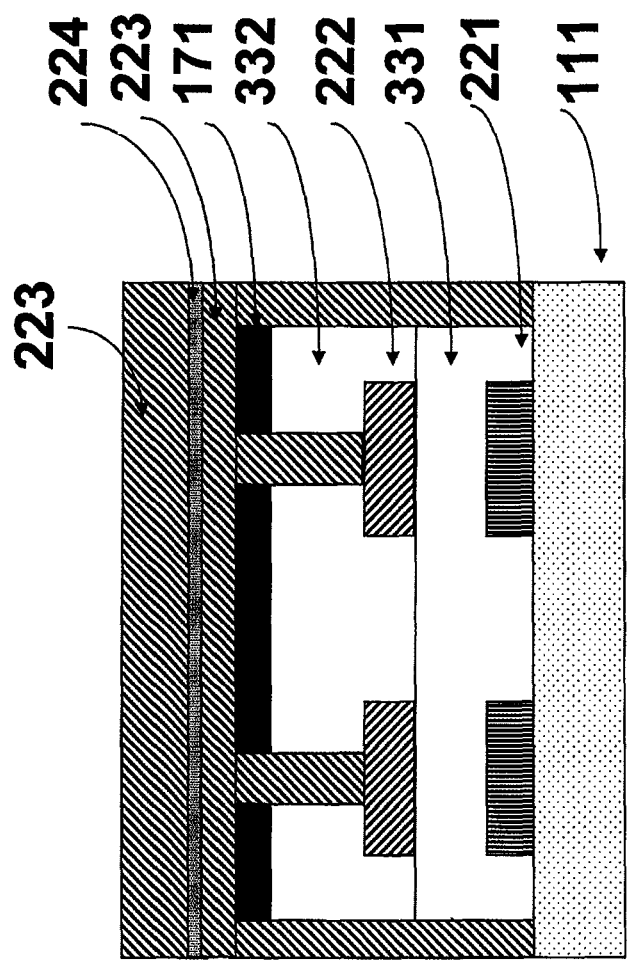
Figure 19:
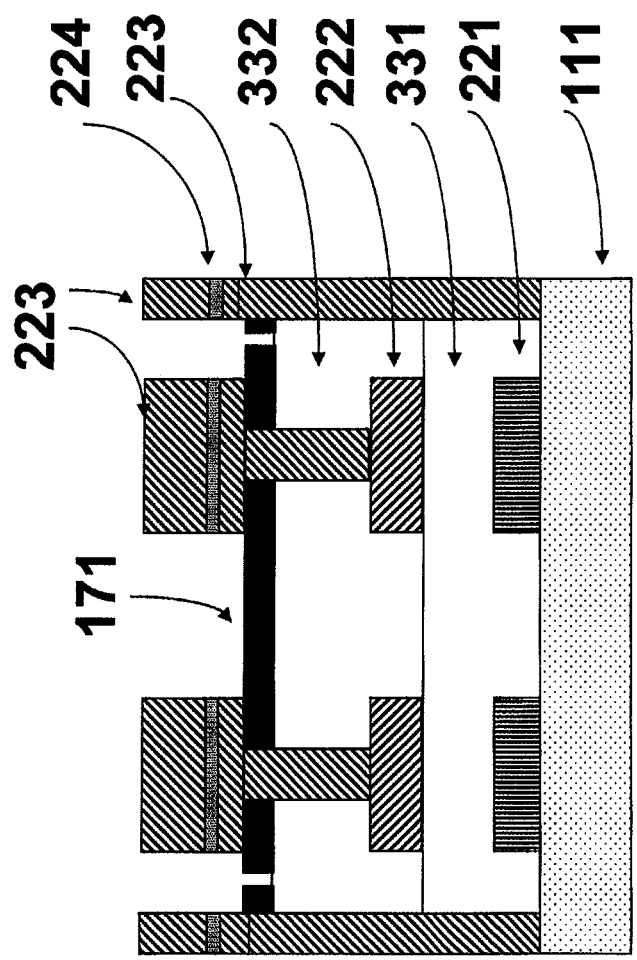
Figure 20A:
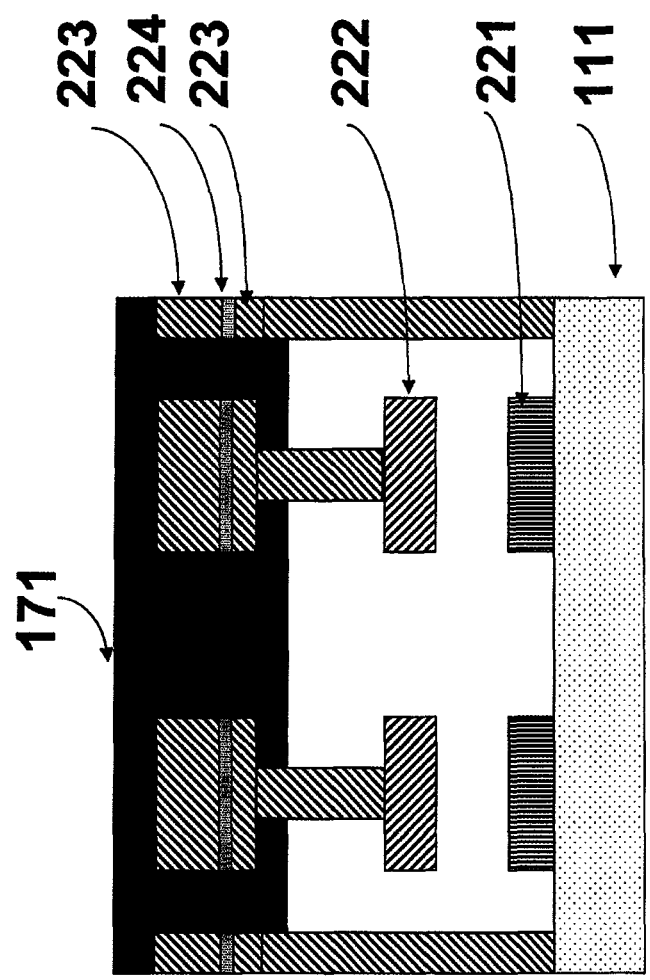

As shown in FIG. 17, a movable material 223 is next deposited to fill in holes and trenches and planarized using CMP. Movable materials 224 and 223 are next deposited in FIG. 18. As shown in FIG. 19, material stack 223/224/223 is subsequently patterned using lithography and etch processes, selective to structural material 171. Small openings in structural material 171 are next created through patterning material 171 using lithography and etch processes and are shown in FIG. 19. Next, as illustrated in FIG. 20A, space materials 332 and 331 are removed via etching, preferably using wet etching or vapor etch process, selective to all other materials present. Another layer of structural material 171 is subsequently deposited and planarized using chemical mechanical polishing. Structures may also be supported in other directions (for example, in horizontal direction vertical to the cross-sectional plane shown in the figures).

Figure 21:
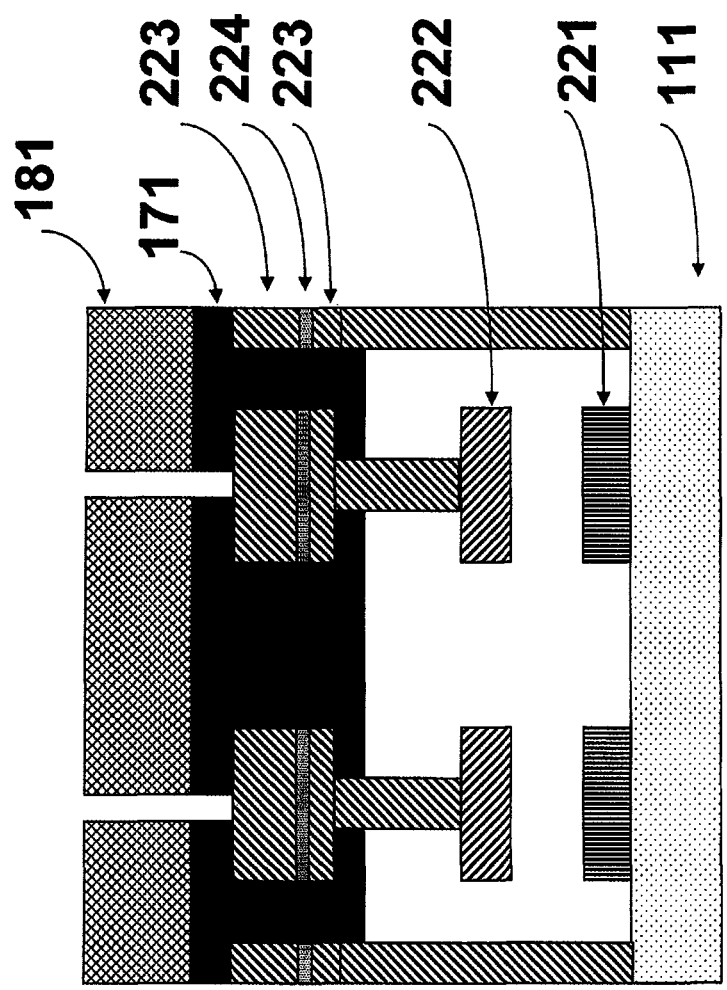
Figure 22:
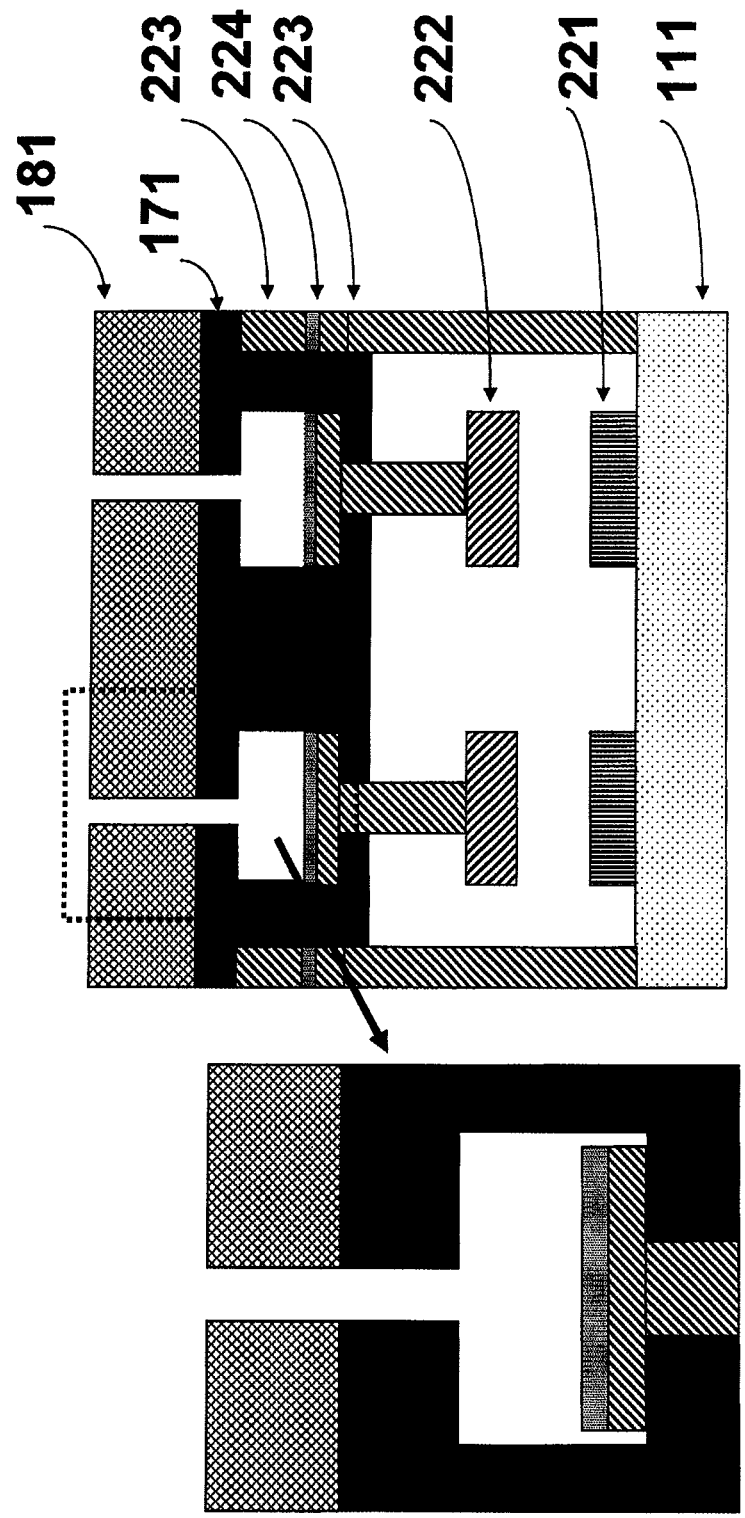
Figure 23:
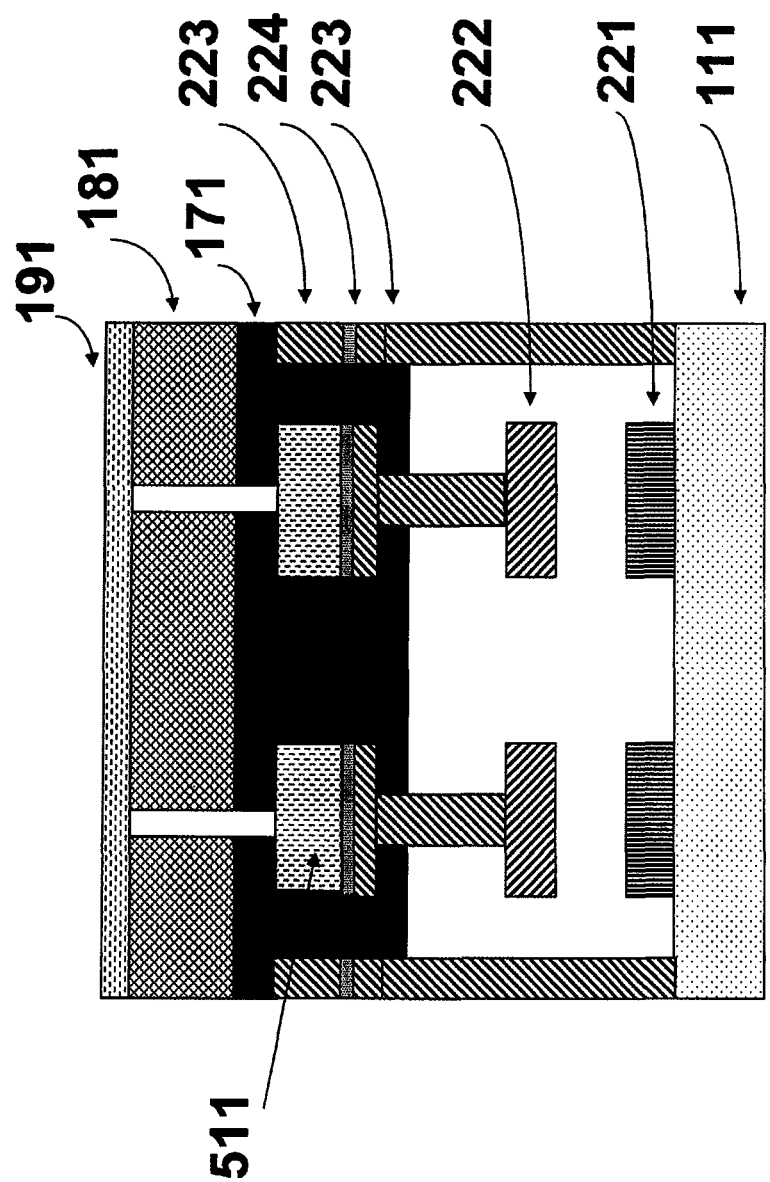
Figure 24:
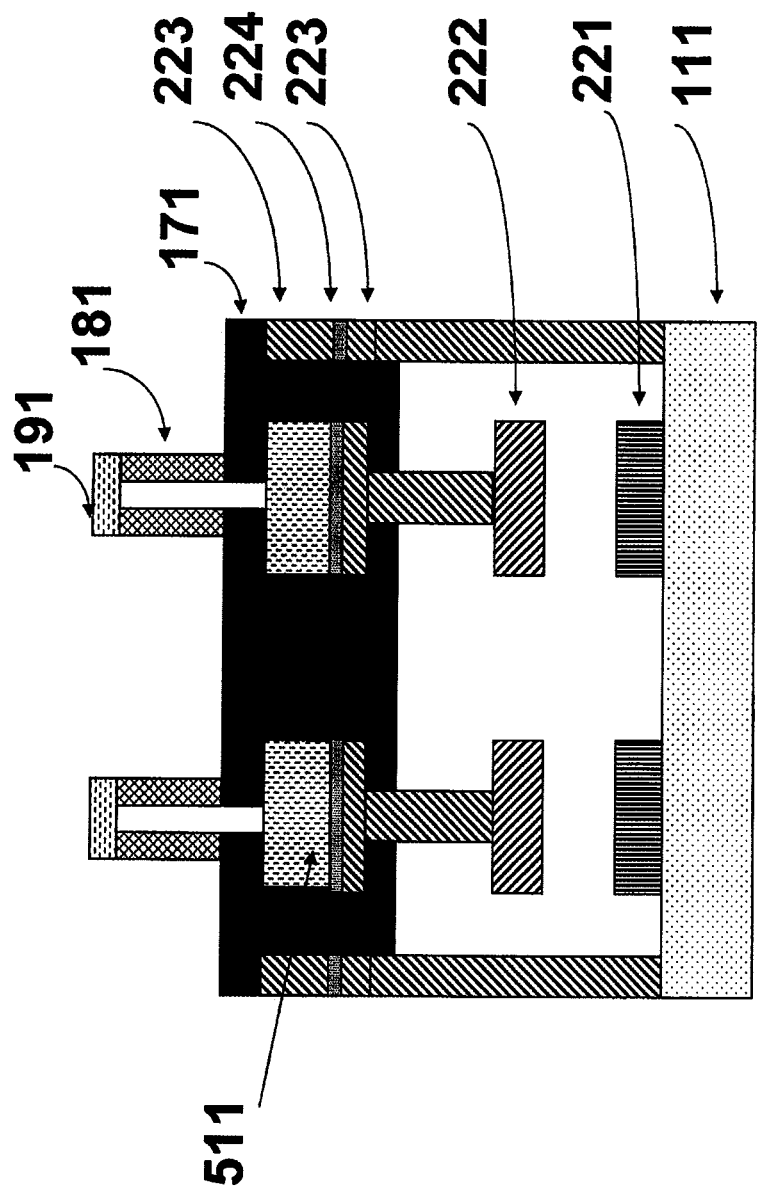
Figure 25:
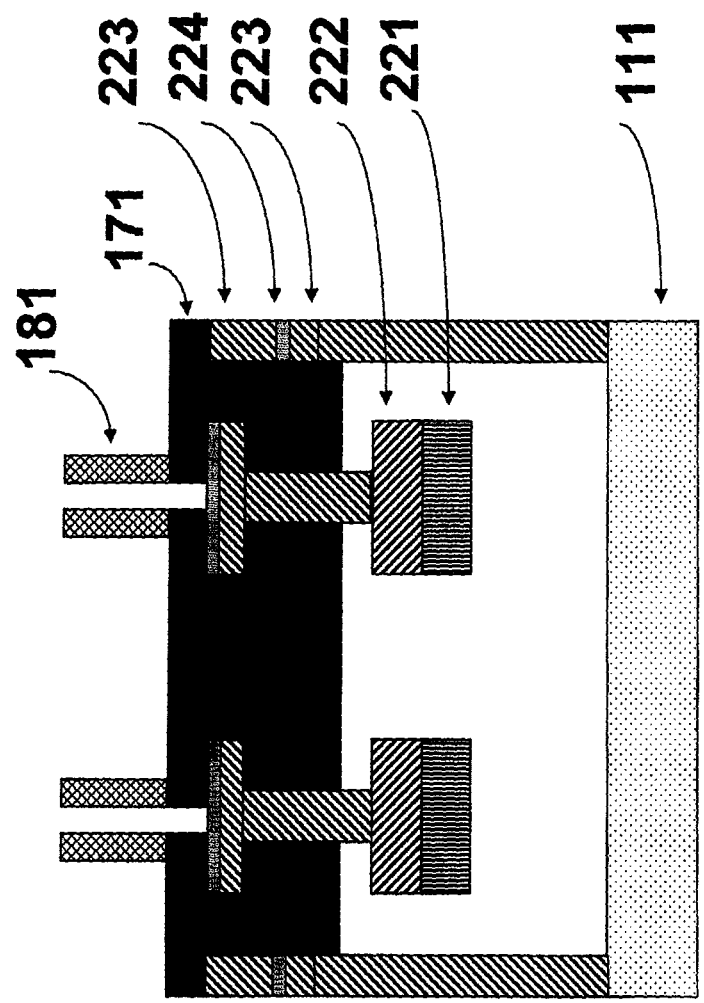

As referred to above, but not illustrated in the drawings, in the case where a thin layer of space material 333 is used, it will also be removed in the same etching step, forming a spacing between movable material 223 and structural material 171, which will help the injector motion. FIG. 20B illustrates a schematic for the case where a space material 333 is used and removed in the etching step, in which the spacing between structural material 171 and movable material 223 is shown and will help the injector motion when it is in operation. In FIG. 21, a structural material 181 is deposited. Next, structural materials 181 and 171 are patterned using lithography and etch processes to form small openings above movable material layer 223, selective to movable material 223. Alternatively, structural materials 181 and 171 can be patterned in separate etch steps. As illustrated in FIG. 22, the top movable material 223 is removed in the areas where there is an opening above it, preferably by wet etching or vapor gas etching, selective to materials 181, 171 and 224, forming a space within structural material 171 (in three sides) and with material 224 at the bottom. This space is the desired micro-container area used to hold the compound to be stored. Next, a short etch is optionally used to etch structural material 171, selective to materials 181, 224, and 223, resulting in a small spacing between the wall of layer 171 and materials stack 224/223 as shown in enlarged portion of FIG. 22. The purpose of this short etch is to form a small spacing to allow for an easier and more smooth motion of injector base plate (materials stack 224/223) during injection action. In FIG. 23, a desired compound 511 is next filled into the micro-containers, followed by application of a desired, taping film 191 to the top surface of layer 181 to seal the micro-containers. Preferably, film 191 is sufficiently thin for easier compound release when pressure is exerted onto it during injection action, while strong enough to keep compound contained before intended release. As illustrated in FIG. 24, materials 191 and 181 are next patterned using lithography and etch processes to form the nozzle of an integrated micro-injector and micro-container. FIG. 24 also serves as a micro-device with an integrated micro-injector and micro-container before compound 511 injection. FIG. 25 illustrates a micro-device after injection of said compound. In FIG. 25, upon an applied force to injector base plate 222 (by push plate 221 in this case), injector base plate 222 pushes up and results in the release of the compound stored in the micro-containers.

Figure 26:
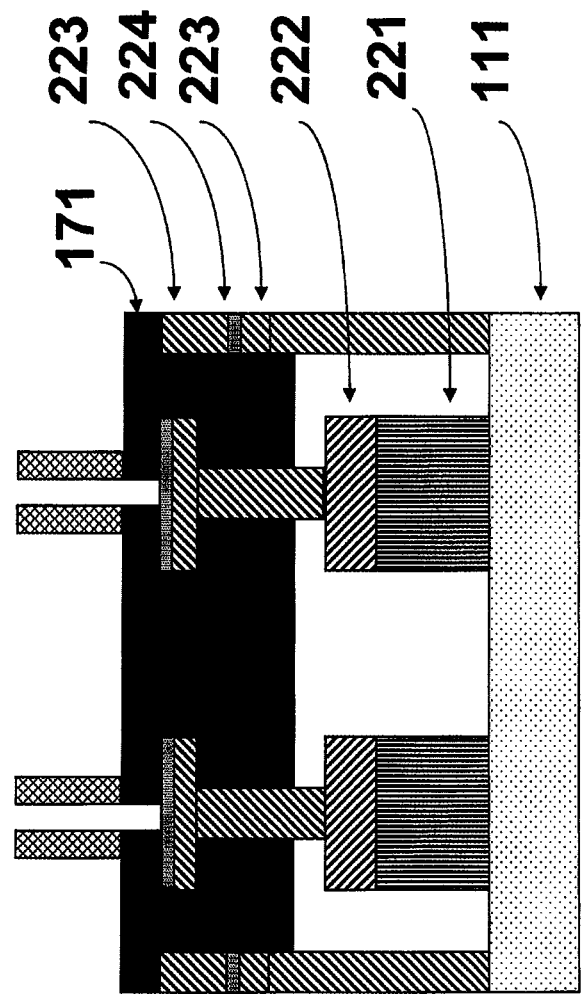

As another embodiment for compound injection, a micro-device with an integrated micro-injector and micro-container using a piezoelectric material as a push plate 221 below an injector base plate 222 is shown in FIG. 26. After application of a desired voltage to the piezoelectric push plate 221, the push plate 221 expands and pushes injector base plate 222 upward, resulting in injection action and compound release.

Figure 27:
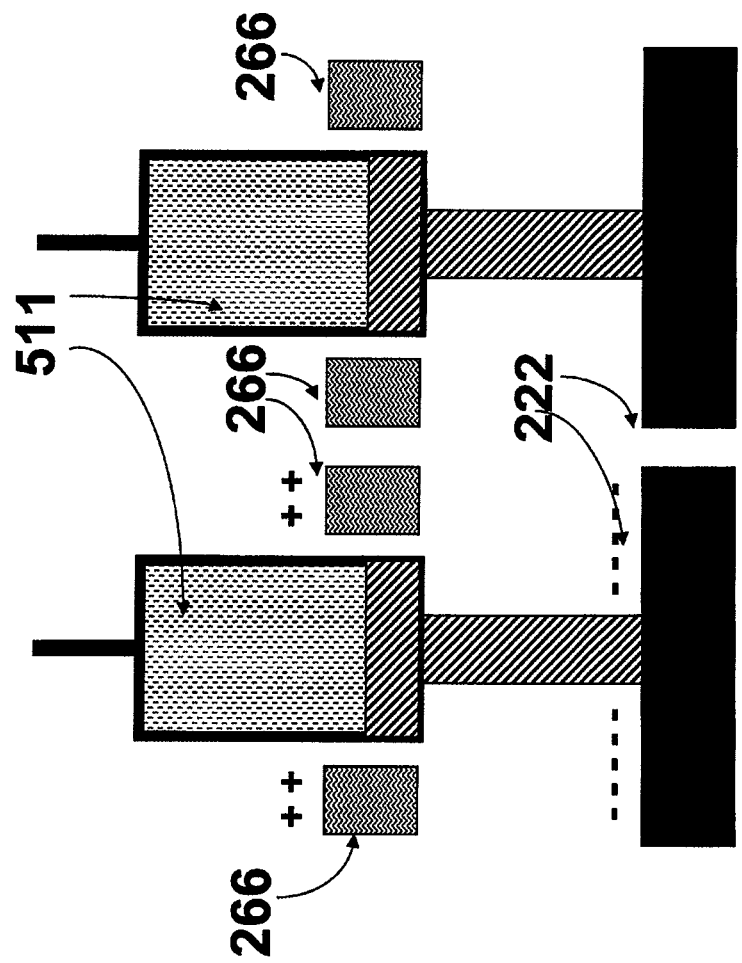
FIG. 27 and FIG. 28 shows micro-injector selection and injection process in a micro-device with an array of micro-containers integrated with micro-injectors and integrated circuits for selecting injector, triggering injector action for the selected injector, and compound release.
Figure 28:
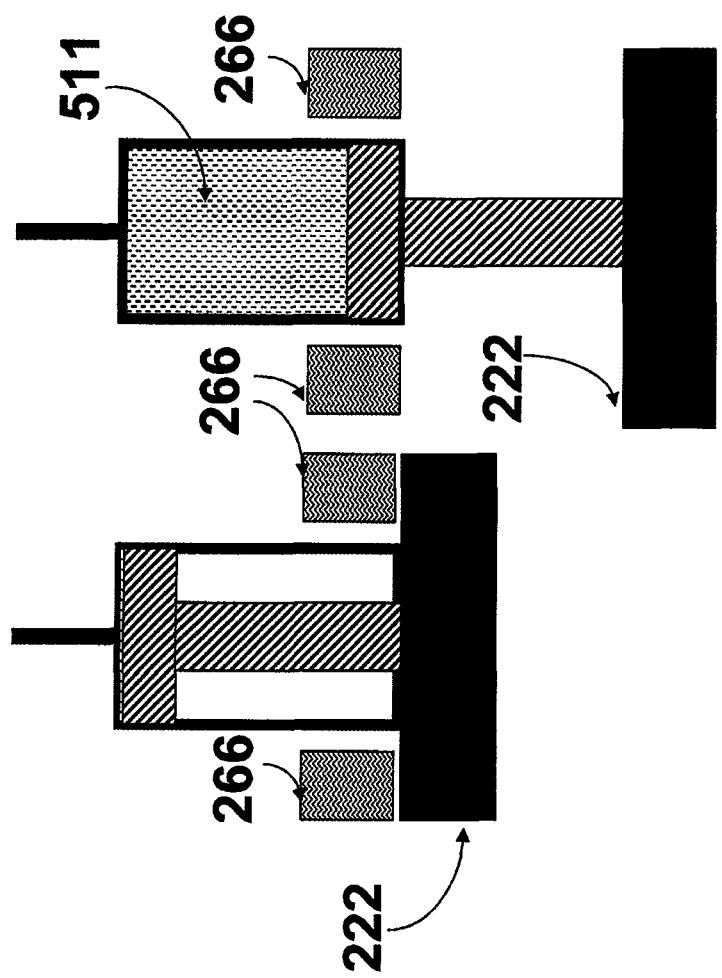

Another major advantage of using a micro-device with micro-containers, micro-injectors, and an integrated circuit integrated on the same unit is the ability to select the micro-container to release compound with time and space control because each micro-container can be interfaced with the integrated circuit and can be instructed by the integrated circuit on when and where to release the compound. For example, a micro-device can have an array of micro-containers, with each micro-container releasing compound based on instructions from the integrated circuit which in turn makes a decision based on a micro-sensor's measurements on a local, living environment. The micro-device can further carry multiple types of compounds stored in the array of micro-containers, with different compounds released in desired time interval and space combinations via integrated circuit instructions to achieve the optimum treatment effects. Specifically, injectors can be individually selected to launch injection action via some applied force to its base plate, triggered by instructions from an integrated circuit on the same micro-device, or by a wireless signal. As one example, FIG. 27 illustrates a micro-device with multiple micro-injectors integrated with micro-containers. Both guide plate 266 and injector bottom plate 222 are connected to integrated circuits via conductive wiring (not shown in the figure). Guide plate 266 serves to select injector to cause injection action when an opposite charge relative to that on the injector plate 222 is applied to it. In FIG. 27, opposite charges are applied to the guide plate 266 and injector plate 222 on the micro-injector on the left. As a result, in FIG. 28, due to the attractive electrical charge force between the injector plate 222 and guide plate 266 for the micro-injector on the left, the injector plate 222 is pulled upward toward the plunger plate 288, resulting in injection action and compound 511 release in the left micro-container, while the micro-injector on the right is not selected and remains inactive.

Figure 29:
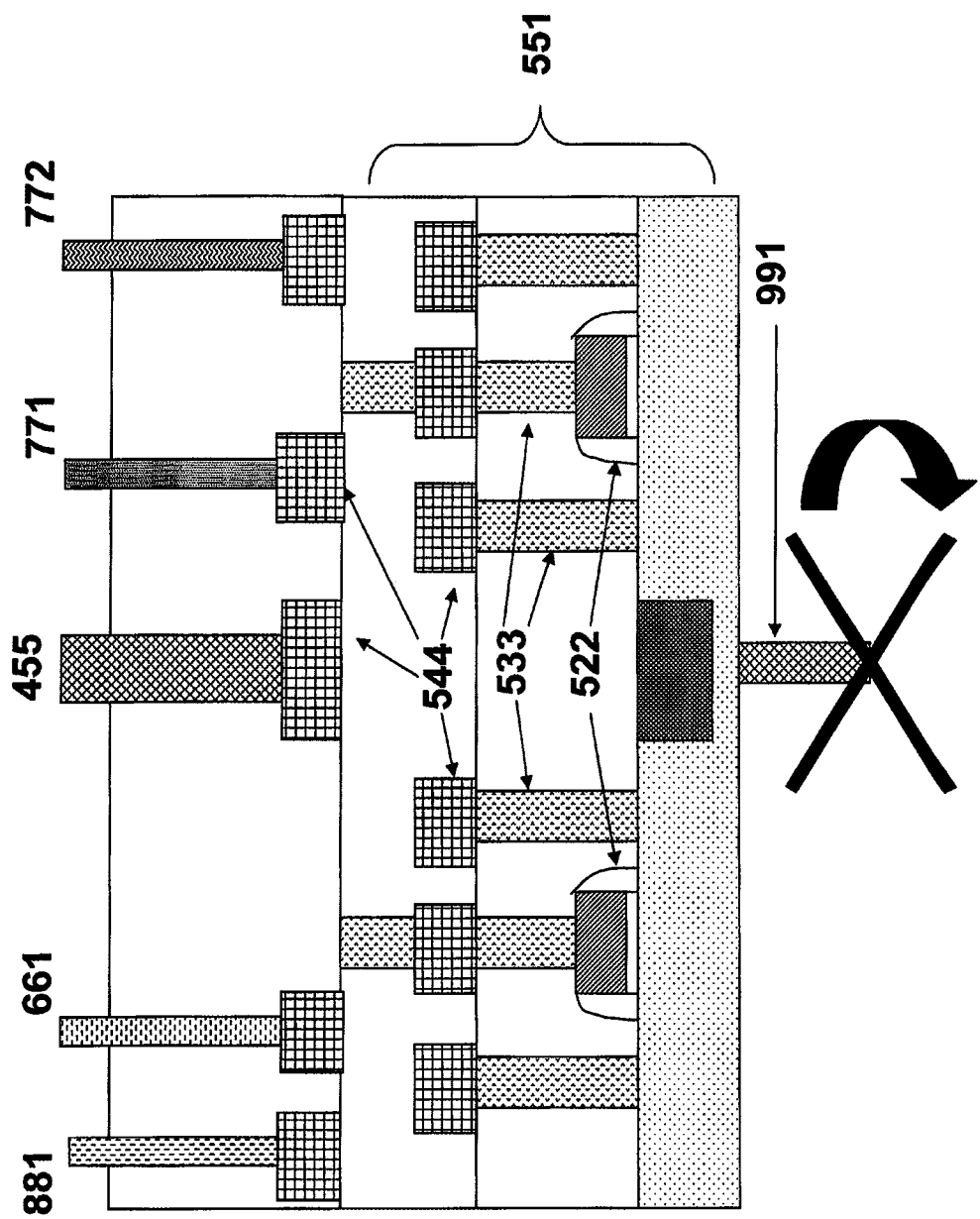
FIG. 29 illustrates a schematic view of a micro-device integrating micro-containers and injectors with integrated circuits such as front end CMOS or BiCMOS integrated circuits with memory and logic functions for data storage, data analysis, data processing, and logic decision making (providing instructions), and other components including sensors, wireless signal transmitter, wireless signal receiver, position sensor, and motion apparatus (motorized propellers in this case).

To enhance the performance and flexibility of micro-devices, in addition to micro-containers and micro-injectors, integrated circuits with data storage and logic processing capabilities and other functional components can also be integrated onto the same substrate using microelectronics fabrication techniques and process flows for biological and medical applications. FIG. 29 shows a cross-sectional schematic view of a micro-device with micro-container integrated with micro-injector 455, sensor 881, signal receiver 771, signal transmitter 772, positioning device 661, and motion device 991 integrated on an integrated circuit 551 with memory and logic processing capabilities for improved performance, with all of them interfaced to the integrated circuit for communication and instruction purposes. The schematic in FIG. 29 shows a number of key components of an integrated circuit including transistors (implanted regions and gate stack 522), metal contact plugs 533, and interconnects 544. The said micro-containers and injectors are electrically connected (interfaced) to the integrated circuits 551 for receiving and executing instructions from the integrated circuits 551. The said integrated circuit 551, which contain both memory and logic functions for data storage, data analysis, data processing and logic decision making such as making injection instruction to release the stored drug, can be fabricated using either CMOS or BiCMOS technologies first, with micro-containers, injectors and other components such as sensors, and signal transmission and receiving components fabricated subsequently on the same substrate. To insure integrity of the integrated circuit 551, processing temperatures for the subsequent micro-containers and injectors are preferably controlled at 400 degrees Celsius or below.

In the above integrated micro-device, the said sensors can detect a wide range of parameters and provide information to the integrated circuits for data analysis and decision making. The signal transmitters and receivers are for wireless communications with outside world (for example for a host computer outside the human body or a doctor). The said motion apparatus such as propeller can be used to position (to move) the micro-device to a desired location. Positioning device can function to determine the relative and absolute locations of the micro-device within the biological body. The integrated circuit serves as a "central commander" to receive data (from sensors and signal receivers), store data, analyze data, make decisions and send instructions to various components (instructing propeller for motions, injectors for compound release, transmitter for signal transmission).

What is claimed is:

1. A method of fabricating a micro-device for biological and medical applications, wherein the method uses microelectronics processes and comprises the following steps:

providing a substrate material having a surface region;

adding a deposit material to the surface region of said substrate material;

patterning said deposit material using photolithography and/or etching processes to form at least a portion of recessed areas;

depositing material S onto the surface region of said deposit material and filling into said recessed areas;

polishing material S via chemical mechanical polishing (CMP) to remove material S from the top surface of said deposit material and leaving sufficient amount of material S in said recessed area coplanar with the top surface of said deposit material;

depositing material C onto the surfaces of material S and said deposit material;

patterning material C using photolithography and/or etching processes;

etching at least portions of existing material S to form a hollow container;

matching a device with nozzle and compound reservoir containing a desired compound;

forcing compound materials into said container through said nozzle; and, etching said reservoir with a material to detach said reservoir from said nozzle to form a micro-device with micro-container filled with the desired compound.

2. A method of fabricating a micro-device for biological and medical applications, wherein the method uses microelectronics processes and comprises the following steps:

providing a substrate material having a surface region;

adding a deposit material to the surface region of said substrate material;

patterning said deposit material using photolithography and/or etching processes to form a portion of recessed areas;

depositing material S onto the surface region of said deposit material and filling said recessed areas;

polishing material S via CMP to remove material S from top surface of said deposit material and leaving sufficient amount of material S in said recessed area coplanar with the top surface of said deposit material;

depositing material C onto the surfaces of material S and said deposit material; patterning material C using photolithography and/or etching processes that are selective to material S;

etching material S that is selective to said substrate, said deposit material, and material C to form a hollow container;

filling container with a desired compound; and, applying a film material to the surface of material C and the top portion of the filled micro-container containing said compound to form a micro-device filled with the desired compound.

3. The method of claim 2, wherein said film material comprises a bio-degradable material.

4. The method of claim 2, wherein said deposit material comprises polysilicon, silicon nitride, silicon oxynitride, or silicon carbide.

5. The method of claim 2, wherein material S, material S1, material S2, and material S3 each comprise silicon dioxide; material C comprises polysilicon, silicon carbide, or silicon nitride; and the wet etching is conducted in a diluted HF solution and vapor etching is conducted using oxygen containing vapor gas.

6. The method of claim 2, further comprising the step of:

(a) fabricating a CMOS or BiCMOS integrated circuit containing both memory and logic processing functions by using microelectronics processes on a desired substrate, or (b) fabricating at least one of the following components around the CMOS or BiCMOS integrated circuit using microelectronics processes: micro-container, micro-injector, signal receiver, signal transmitter, sensors, positioning device, and motorized propeller.

* * * * *